United States Patent
Richert et al.

(10) Patent No.: US 11,668,321 B2
(45) Date of Patent: Jun. 6, 2023

(54) BLOOD PUMP

(71) Applicant: Berlin Heart GmbH, Berlin (DE)

(72) Inventors: Hendryk Richert, Berlin (DE); Oliver Peters, Berlin (DE)

(73) Assignee: Berlin Heart GmbH, Berlin (DE)

( * ) Notice: Subject to any disclaimer, the term of this patent is extended or adjusted under 35 U.S.C. 154(b) by 2 days.

(21) Appl. No.: 17/057,423

(22) PCT Filed: May 27, 2019

(86) PCT No.: PCT/EP2019/063605
§ 371 (c)(1),
(2) Date: Nov. 20, 2020

(87) PCT Pub. No.: WO2019/228958
PCT Pub. Date: Dec. 5, 2019

(65) Prior Publication Data
US 2021/0205602 A1    Jul. 8, 2021

(30) Foreign Application Priority Data

May 28, 2018  (EP) ..................... 18174614

(51) Int. Cl.
*F04D 29/52* (2006.01)
*A61M 60/237* (2021.01)
(Continued)

(52) U.S. Cl.
CPC .......... *F04D 29/528* (2013.01); *A61M 60/17* (2021.01); *A61M 60/221* (2021.01);
(Continued)

(58) Field of Classification Search
CPC .... A61M 60/42; A61M 60/82; A61M 80/816; A61M 80/237; A61M 80/824;
(Continued)

(56) References Cited

U.S. PATENT DOCUMENTS 5,840,070 A * 11/1998 Wampler ............... H02K 41/03
                                                    417/423.1
5,957,672 A *  9/1999 Aber .................... A61M 60/825
                                                    417/423.12
(Continued)

FOREIGN PATENT DOCUMENTS

WO   WO 00/64030      10/2000
WO   WO 2008/017289 A2   2/2008
(Continued)

OTHER PUBLICATIONS

International Search Report with English translation, issued in International Application No. PCT/EP2019/063605, dated Jul. 31, 2019, pp. 1-6, European Patent Office, Rijswijk, Netherlands.

*Primary Examiner* — Kenneth J Hansen
(74) *Attorney, Agent, or Firm* — Crowell & Moring LLP

(57) ABSTRACT

A pump is provided with a housing and with an upstream inlet and a downstream outlet and a fluid channel with a channel axis, said fluid channel being arranged between the inlet and outlet. A rotor which can be brought into rotation by way of a motor is arranged within the fluid channel. Furthermore, a sensor arrangement is provided which can detect an inclination of the rotation axis of the rotor.

19 Claims, 6 Drawing Sheets

(51) Int. Cl.
  *A61M 60/226* (2021.01)
  *A61M 60/419* (2021.01)
  *A61M 60/221* (2021.01)
  *A61M 60/824* (2021.01)
  *A61M 60/825* (2021.01)
  *A61M 60/82* (2021.01)
  *F04D 29/047* (2006.01)
  *F04D 29/18* (2006.01)
  *A61M 60/17* (2021.01)
  *A61M 60/816* (2021.01)
  *F04D 15/00* (2006.01)

(52) U.S. Cl.
  CPC ........ *A61M 60/226* (2021.01); *A61M 60/237* (2021.01); *A61M 60/419* (2021.01); *A61M 60/816* (2021.01); *A61M 60/82* (2021.01); *A61M 60/824* (2021.01); *A61M 60/825* (2021.01); *F04D 15/0088* (2013.01); *F04D 29/0476* (2013.01); *F04D 29/181* (2013.01); *A61M 2205/0238* (2013.01); *A61M 2205/3317* (2013.01); *A61M 2205/3327* (2013.01)

(58) Field of Classification Search
  CPC .. A61M 80/825; F04D 29/048; F04D 29/058; F04D 29/181; F04D 29/0476; F04D 13/026
  See application file for complete search history.

(56) References Cited

U.S. PATENT DOCUMENTS

| | | | |
|---|---|---|---|
| 6,581,476 B1* | 6/2003 | Fremerey | A61M 60/10 73/861.77 |
| 9,393,355 B2* | 7/2016 | Peters | A61M 60/818 |
| 2001/0002234 A1* | 5/2001 | Woodard | F04D 29/2261 415/182.1 |
| 2012/0130152 A1 | 5/2012 | Ozaki et al. | |
| 2013/0121821 A1 | 5/2013 | Ozaki et al. | |
| 2014/0275723 A1* | 9/2014 | Fritz, IV | F04D 27/001 600/16 |
| 2016/0235898 A1* | 8/2016 | Yanai | F04D 13/064 |

FOREIGN PATENT DOCUMENTS

| | | |
|---|---|---|
| WO | WO 2011/063994 A1 | 6/2011 |
| WO | WO 2019/033012 A1 | 2/2019 |

* cited by examiner

BLOOD PUMP

CROSS-REFERENCE TO RELATED APPLICATIONS

This application is a 371 nationalization of international patent application PCT/EP2019/063605 filed May 27, 2019, which claims priority under 35 USC § 119 to European patent application 18174614.0, filed May 28, 2018. The entire contents of each of the above-identified applications are hereby incorporated by reference.

BRIEF DESCRIPTION OF THE DRAWINGS

There are shown.

DETAILED DESCRIPTION

Figure 1A:
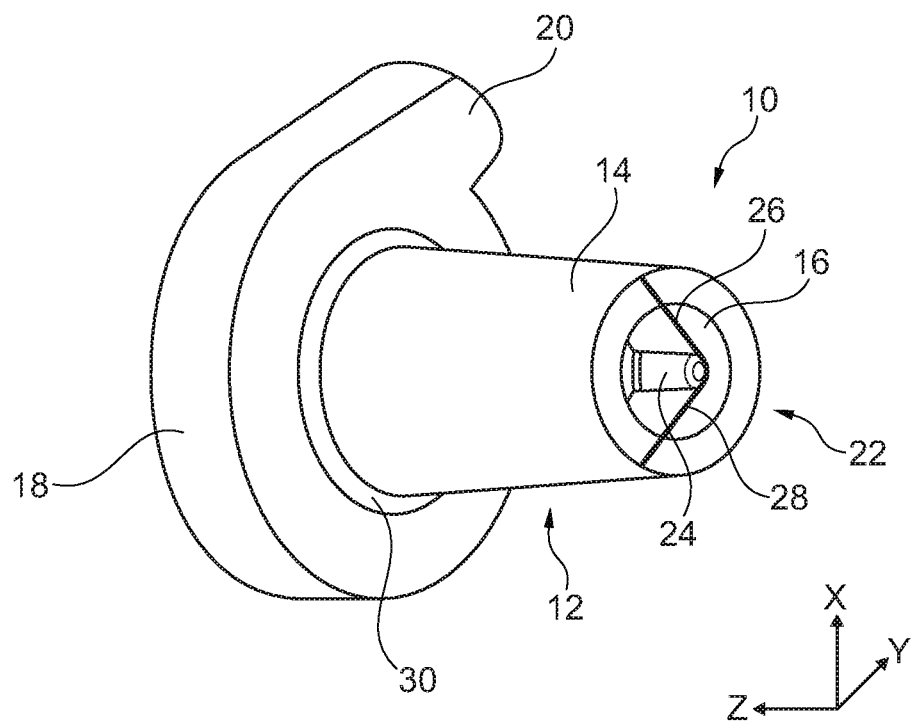
FIG. 1A a schematic view of an axial pump with a tangential outlet.

The subject-matter of the present invention is a pump, preferably a blood pump, for the application in heart assistance systems. In particular, the use as a ventricular assist device (VAD) for the left ventricle (LVAD) or the right ventricle (RVAD) or within the framework of a system for both ventricles (BiVAD).

The monitoring of the flow of the pumped fluid or other of the pump parameters is of particular importance with blood pumps. In order to be able to exactly set the pump output, either a monitoring of pump parameters by way of sensors is necessary or an estimation of the parameters and a corresponding evaluation.

An important parameter is the estimation or the measurement of the flow which is delivered by the pump. Concerning blood pumps, the flow estimation or the flow measurement is a precondition for the physiological closed-loop control in a pump. For example, ultrasound sensors or ultrasound measurements can be used as flow sensors. In actively magnetically mounted pumps, such as for example the HeartMate III of Thoratec, a positional change of the rotor with respect to the housing within a plane transverse to the inlet axis is used for the flow estimation.

A flow estimation on the basis of the deflection of a pump rotor by way of Hall effect sensors in the case of a magnetically actively mounted radial pump is described in WO 2017/015268A1. The rotor deflection must be permanently monitored, in order to be able to ensure the operation of the pump. The closed-loop control of actively mounted pumps is cumbersome and demands numerous control mechanisms.

A method for determining a tilting of rotor of a rotation machine, with the help of which a magnetically actively mounted motor or its position between the two upstream and downstream guide vanes is determined, is described in WO 2009/132707A1. Here too, it is the case of an actively mounted pump whose monitoring is complicated.

It is the object of the present application to provide an alternative blood pump which has a less complex construction. Furthermore, a method of using such a pump for a flow estimation is also put forward.

The pump comprises a housing with an upstream inlet and a downstream outlet. A fluid channel with a first channel axis is present between the inlet and the outlet, along which fluid channel the fluid to be delivered is trans-ported from the inlet in the direction of the outlet. A rotor with an upstream end and a downstream end is located downstream of the inlet, wherein the rotor comprises a blading for the delivery of the fluid. At its upstream end, the rotor is mounted by way of a mechanical or hydrodynamic bearing.

In the case of a mechanical bearing, an inlet guide vane can be arranged in or outside the fluid channel upstream of the rotor, wherein the inlet guide vane is held by way of struts which hold the inlet guide vane, or by way of blades which hold the inlet guide vane and which impart a significant swirl flow upon the fluid to be delivered. For example, a bearing head can be arranged at the upstream end of the rotor, and a bearing calotte which corresponds to this can be arranged in the inlet guide vane (or vice versa). Details concerning the respective bearings can be derived from the applications EP 18 164 553.2 and PCT/EP2017/074796, these being adopted in their entirety as a constituent of this application.

In the case of a hydrodynamic bearing, a fluid channel narrowing can be arranged upstream of the rotor, so that a hydrodynamic bearing forms between the rotor and the fluid channel narrowing in the direction of the channel axis.

The part of the fluid channel in which the rotor is arranged comprises a tubular section with an essentially circular cross section. The fluid channel can further comprise a volute chamber, a spiral chamber or an annular chamber, connecting onto the tubular section, in which the outlet is arranged. The rotor can extend out of the tube to into the annular chamber, the spiral chamber or volute chamber or can be arranged exclusively in the tubular section.

The pump according to the application is an axial machine, i.e. the rotor delivers the blood in an axial manner and initiates a pressure build-up and the fluid is pumped out of the pump on account of a pressure gradient. In numerous variants, the blading may suitably be a spiral-like blading. The spiral can have less than one complete revolution around the rotor body, a complete revolution around the rotor body or more than one revolution around the rotor body and in numerous embodiments the rotor has more than one spiral, for example 2 or 3 spirals. Therein, the pitch between the spirals increases from the upstream end of the rotor to the downstream end of the rotor. In numerous embodiment examples, the blading extends from the upstream end of the rotor to half the rotor and in other embodiments the blading can extend further to the downstream end.

The rotor is brought into rotation by way of a motor which is arranged in the housing. The motor stator revolves around a motor rotor which is arranged within the rotor, and drives this.

As initially mentioned, the upstream end of the rotor is held by way of a mechanical bearing or a hydrodynamic bearing. Additionally to this bearing, the pump comprises a passive magnetic bearing, with the help of which the downstream part of the rotor is held in the desired position. Here, it is preferably the case of a passive magnetic radial bearing which radially mounts the rotor, axially biases this and presses upon the mechanical or hydrodynamic bearing. A component of the passive magnetic bearing is arranged in the rotor and for example can be a magnetic ring or cylinder, or several rings/cylinders in a squeeze field arrangement or Halbach arrangement. The counter-piece to this is arranged in the housing and in some embodiment examples can run around the ring which is arranged in the rotor. In order to achieve a biasing, the magnetic bearing components which are arranged in the housing and the rotor, can be axially offset to one another along the channel axis. Alternatively or additionally to the passive magnetic bearing, a hydrodynamic bearing or a flexible mechanical bearing can be present.

The pump further comprises a sensor arrangement for detecting an inclination of the rotor axis of the rotor. The sensor arrangement can detect a deviation of the rotor axis from the channel axis. The fluid channel forms a fixed coordinate system in which the channel axis fixedly lies, and for example forms the z-axis of a Cartesian coordinate system. The rotor which rotates about the rotation axis can experience a deflection out of the z-axis on running operation of the pump, i.e. whilst the rotor is driven by the motor. Thus for example the flow to be delivered can effect a tilting of the rotor about the contact point in the region of the mechanical or hydrodynamic bearing. This deflection can then be detected and be used as an estimation of the pressure difference in the volute and for the delivered flow. Furthermore, the tilting of the rotor, i.e. the deviation of the rotation axis from the channel axis can be detected in a time-resolved manner and for example the change of the turbulence (thrombi growth, entrained thrombi) or other physiological activities (pulse, breathing, movement) as well as irregularities can be detected on the basis of the frequencies of the movement of the rotor.

Since the pump is a passively mounted pump which in some embodiment examples has no active closed-loop control of the mounting, the construction of the pump is very simple. The sensor arrangement is only used in order to determine the tilting of the rotor with respect to the housing and does not need to fulfil any function of relevance to the reliability. However, the tilting can also be used in order to increase the patient safety. It is merely the rotational speed of the motor which needs to be actively closed-loop controlled.

Concerning the sensor arrangement, this is preferably a sensor arrangement which detects and evaluates a magnetic field which is produced by a component of the rotor or by the rotor itself. It is preferable for the sensor arrangement to be arranged symmetrically about the channel axis. I.e. either a sensor is arranged along the channel axis or a multitude of sensors is arranged in a plane perpendicularly to the channel axis about this axis, preferably in a symmetrical manner.

Alternatively or additionally, the sensor arrangement can be arranged downstream of the rotor. Given an arrangement downstream of the rotor, it is possible in a simple way and manner to use a magnetic field of the rotor which runs in the direction of the channel axis for evaluating the tilting of the rotor. Since the sensor arrangement is preferably arranged in a plane transverse to the channel axis, the direction of the running magnetic field of the rotor becomes measurable in a precise manner and hence the accuracy of the detection of the tilting of the rotor is very high. Preferably, at least one magnetoresistive sensor (e.g. an anisotropic magnetoresistive (AMR), giant magnetoresistive (GMR) or tunnel magnetoresistive (TMR) sensor) which can determine magnetic field strength or direction, or several Hall effect sensors, such as for example three or more Hall effect sensors, can be used in such the sensor arrangement. The application of fluxgate or magnetoinductive sensors is also possible. In the case of a magnetoresistive sensor, it is precisely only one sensor which is necessary (however one can also use more than one sensor). This one sensor detects the direction of the magnetic field for example along the channel axis, and the direction of the magnetic field within the plane transverse to the channel axis. The resulting magnetic field vector can be used in order in order to detect a tilting of the rotor with respect to the channel axis, since the direction of the magnetic field of the rotor is shifted with respect to the magnetic field direction which runs in the idle state. The tilting of the rotor can be determined from this magnetic field shift. In the case of several Hall effect sensors, for example a sensor array of three or more sensors can be applied within a (preferably single) plane transverse to the channel axis. The individual Hall effect sensors detect the magnetic field strength along the direction of the channel axis. A tilting of the rotor can be determined from the combination of the signals of the several Hall effect sensors, since a tilting of the rotor entails a tilting of the magnetic field direction which is produced by the rotor. Alternatively or additionally to the already aforementioned sensor types, fluxgate sensors or induction coils or force sensors loaded with magnets can also be used.

Alternatively or additionally, the sensor arrangement can be designed in a manner such that it is designed for the differential measuring of the magnetic field. Herein, sensors are each arranged in pairs in a plane transverse to the channel axis, so that a tilting in the direction of the first sensor of the sensor pair at this first sensor leads to a magnetic field increase, whereas the second sensor experiences a weakening of the magnetic field. A particularly accurate detection of the magnetic field can be effected by way of the differential measuring of the magnetic field. The differential measuring further moreover suppresses locally uniform interference fields such as for example the earth's magnetic field.

Alternatively or additionally, the rotor comprises a magnetic flux concentrator which is preferably arranged in the region of the downstream end of the rotor. Inasmuch as the sensor arrangement is a sensor arrangement for detecting a magnetic field, a flux concentrator, for example of soft iron can increase the magnetic flux in the direction of the channel axis and thus improve the measuring accuracy. Alternatively or additionally, the rotor upstream of the flow concentrator can comprise a flux generator, in order to generate the magnetic field to be concentrated in the rotor. In particular, a component of the passive magnet bearing which is arranged in the rotor lends itself as a flux generator. The flux generator is preferably a magnetic ring or a magnetic disc/cylinder which is arranged around the rotation axis of the rotor.

Alternatively or additionally, the rotor tapers towards its downstream end. By way of the tapering, one the one hand flow-technical advantages can be effected on delivering the fluid, and on the other hand a concentration of the magnetic field in the region of the tapered end can be achieved. By way of this, the magnetic field strength along the rotation axis is increased, which in turn increases the measuring accuracy. In a variant, the rotor can have for example a teardrop-shape. In other variants, the rotor at its downstream end can run for example in a manner of a truncated cone or in a cone-like manner.

Alternatively or additionally, a mechanical or hydrodynamic backup bearing which restricts the downstream end of the rotor in its movement freedom is arranged on the housing. The backup bearing can be arranged for example in a manner such that the rotor is mechanically or hydrodynamically blocked given too large a tilting. The mechanical backup bearing can have the nature of a ring which projects out of the downstream part of the housing and on which the downstream end of the motor abuts given too high a tilting. By way of this, a more reliable operation of the pump is ensured.

As already mentioned, the fluid channel can alternatively or additionally merge into an outlet chamber, wherein the outlet axis of the outlet is inclined at an angle with respect to the channel axis, preferably runs essentially perpendicularly thereto. By way of the tangential outlet, a shortening of the pump is effected and the working region of the pump is positively influenced. In some embodiments one can envisage the blading of the rotor not extending into the outlet chamber but merely into the tubular section. Although until now only a single outlet has been mentioned, the pump can comprise further outlets, for example two or more outlets.

As initially described, the passive magnetic bearing is a passive magnetic radial bearing. This can be arranged in the region of a tubular section, preferably downstream of a motor stator. A radial bearing is to be understood in that the bearing is mounted in a radially stable manner. The bearing however can also be designed in a manner such that it is axially instable.

A tilting of the rotor can be detected by way of the sensor arrangement. It is, however, not necessary to detect the tilting of the rotor in degrees, but it is sufficient to detect the magnetic field changes. The position of the downstream end of the rotor and hence the tilting can be determined from the measured magnetic field changes. One can envisage the magnetic field change in combination with the speed and the electricity consumption of the motor and an estimated viscosity being converted into a pressure difference and/or a delivered flow on the basis of tables which are stored in the pump controller, or of simple, multi-dimensional approximations with polynomials of the nth degree (preferably not greater than 4). Furthermore, the movement of the rotor, in particular its movement frequencies can be used in order to detect thrombi in the region of the pumps and to estimate the viscosity of the blood. Furthermore, the (possibly time-resolved) tilting can be evaluated, in order to recognise a wearing of the upstream mechanical bearing, a magnetic bearing or the motor components. Furthermore, the tilting can be used for estimating the pressure, or a composed characteristic value can be used, wherein the composed value is composed of two or more of the subsequent variables: flow, pressure, viscosity, deposits and wear.

Alternatively or additionally, one envisages the sensor arrangement being arranged in a manner such that the magnetic field of the motor magnets can be neglected or is even isolated. The motor magnetic field is not then used for the detection.

A few embodiment examples are explained in more detail in the subsequent figures.

The pump 10 which is represented in FIG. 1A considered from the outside comprises a housing 12 which on the one hand comprises a tubular section 14 with an inlet 16; and further an outlet chamber 18 with an outlet 20. Furthermore, a bearing stator 24 which is held in a central manner and coaxially to the tubular section 14 by way of struts 26 and 28 can be recognised on the inlet region 22 of the pump 10. The bearing stator 24 forms the stationary part of a mechanical bearing, which will be yet dealt with in more detail. The struts 26 and 28 are selected thinly and have such a cross section that these essentially do not change an inflowing fluid with regard to its flow behaviour. For example, the struts can have a thickness which is measured in the xy-plane of 0.5-3 mm, a length which is measured in the z-direction of 2-10 mm and an essentially oval or circularly round profile. The struts essentially run along the z-direction.

Alternatively to this, the bearing stator 24 can be held for example by blades which impart a swirling flow upon the fluid to be delivered. The blades in some embodiments have a curvature (similarly to a rotor blading), in order to impart a pre-rotation upon the fluid. The blades can have a length of up to 15 mm. In the state of the art, one often speaks of upstream guide vane.

The outlet 20 is configured in a manner such that this can be connected to a graft or to a silicone cannula for example by way of a connector. Furthermore, a sewing ring connector 30 can be recognised on the pump, by way of which connector the pump can be fastened to a sewing ring which is arranged on the heart. The tubular section 14 of the housing 12 is pushed into an opening, for example of the left ventricle, whereas a graft which is connected to the outlet or to an outlet cannula is connected to the aorta or for example to the subclavian artery.

The pump 10 which is represented here is an axial machine with a tangential outlet 20; i.e. the rotor delivers the blood in the axial direction and increases the pressure of the fluid downstream, in order to deliver the fluid. In other embodiment examples, the pump however can be a radial machine, concerning which the rotor accelerates the blood to the outside.

The outlet chamber 18 can be an annular chamber which with respect to the fluid channel of the tubular section 14 has no radial extension; a spiral chamber which has a radial extension of the outlet chamber with respect to the fluid channel of the tubular section; or a volute chamber which has a radial as well as axial widening of the fluid channel of the tubular section towards the outlet 20.

Figure 1B:
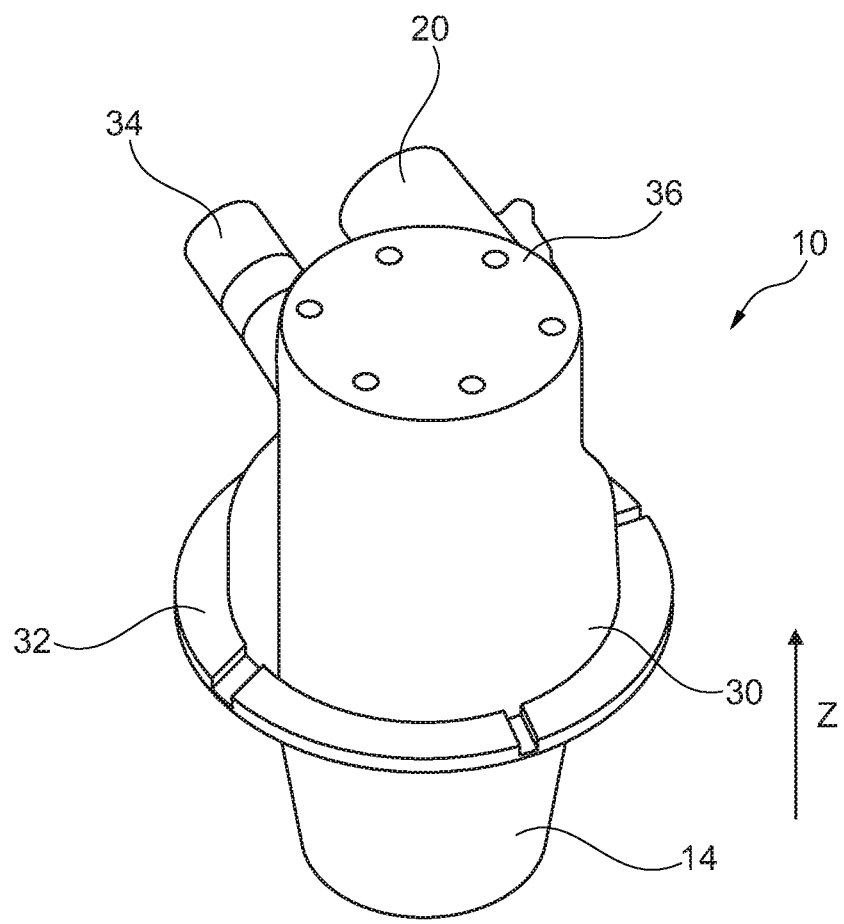
FIG. 1B a schematic view of the rear side of the pump which is shown in FIG. 1A.

In FIG. 1B, the pump 10 which is represented in FIG. 1A is shown in a different view. Here too, the tubular section 14 can be seen. Furthermore, a sewing ring 32 which corresponds to the sewing ring connector 30 and which in the implanted state is connected to a ventricle of the heart is drawn. The outlet 20 is well recognisable. Apart from the outlet 20, furthermore an exit for the driveline 34 can be recognised. Electrical energy for the operation of the pump, but also control signals are sent to the pump by way of the driveline. Signals which are detected in the pump and which for example are received by the sensor arrangement are led further to an external control unit. Considered in the z-direction, a housing part which serves as a chamber 36 for the sensor arrangement connects onto the outlet chamber. This means that the sensor arrangement is held in the chamber 36, but that the sensor arrangement does not lie in the fluid channel.

Figure 2:
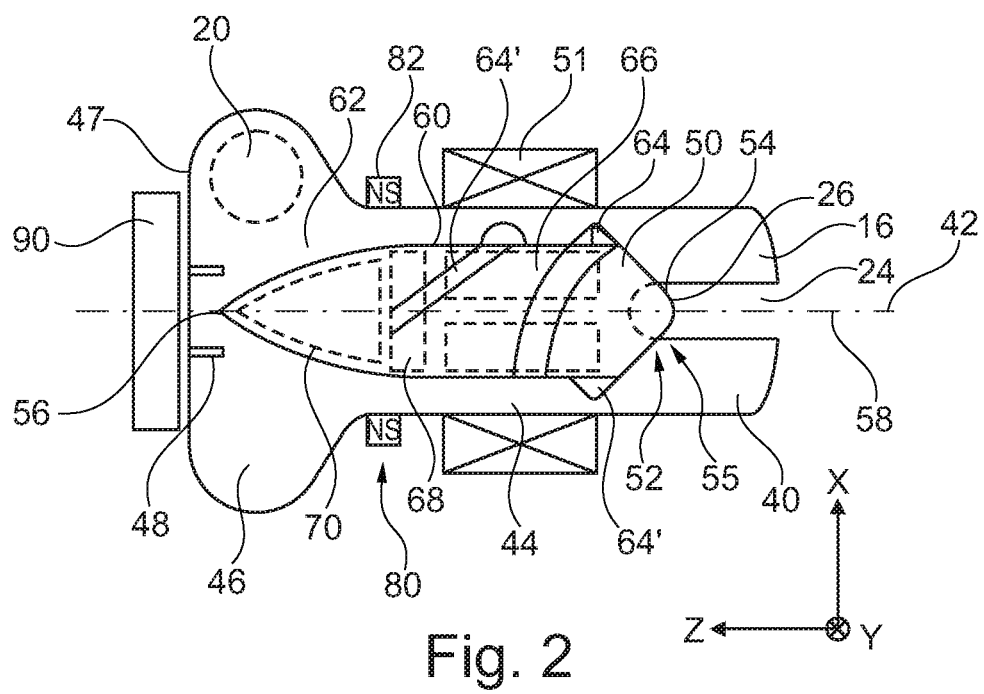
FIG. 2 a longitudinal section through the pump which is shown in FIG. 1A (schematic)

In FIG. 2, a longitudinal section along the xz-plane of the pump 10 of FIG. 1A is represented. A fluid channel 40 with a channel axis 42 which here is selected such that it runs along the z-axis extends between the inlet 16 and the outlet 20. A rotor 50 which can be brought into rotation by way of a motor stator 51 which does not lie in the fluid channel is arranged in the fluid channel. The fluid channel 40 comprises a cylinder-shaped section 44 which merges into a spiral chamber 46. It can be recognised that the diameter of the outlet chamber along the x-axis is larger than the diameter of the cylinder-shaped section 44.

Furthermore, an annular stop 48 which serves as a mechanical backup bearing and which will be yet dealt with in more detail is located on the downstream end of the fluid channel 40, in the region of the spiral chamber wall 47. A sensor arrangement 90 which will likewise be yet explained in more detail is located outside the fluid channel and within the housing, down-stream of the downstream wall 47 of the housing 12.

In FIG. 2, the bearing stator 24 can be easily recognised. The bearing stator 24 at its downstream end 26 ends in a bearing calotte which can be coated or designed with a hard ceramic based on carbide or with a diamond. For example, bearing calottes are to be found for example in PCT/EP2017/074796 which is adopted in its entirely as a constituent of this application.

The rotor 50 at its upstream end 52 comprises a bearing component 54 which corresponds to the bearing calotte 26 and which for example can be a diamond-coated ball or a ball segment which is manufactured from diamond. The mechanical bearing 55 which is formed from the components 54 and 26 serves as an axial/radial bearing since the rotor 50 during the delivery of the fluid is pressed by the fluid pressure onto the bearing calotte 26. Further-more, the mechanical bearing 55 serves as a contact point for the rotor 50, about which the rotor 50 itself can tilt. Given a tilting of the rotor out of the channel axis, the downstream end 56 of the rotor is tilted in the x-direction or y-direction. Whereas in FIG. 2 the rotation axis 58 of the rotor 50 coincides with the channel axis 42, the rotation axis 58 can differ from the channel axis 42 on pump operation, so that the two form an angle α. With regard to the bearing 55 of the components 26 and 54 which is shown here, this bearing forms the intersection point between the two straight lines.

The rotor 50 widens from the bearing component 54 in the z-direction, increases in its dimension which is measured in the xy-plane and runs out in a cylinder-shaped section 60. This cylinder-shaped section 60 subsequently tapers into a cone-shaped or truncated-cone-shaped section 62. The transition between the cylinder-shaped section 60 and the truncated-cone-shaped section 62 still lies within the cylinder-shaped section 44, but in other embodiments can begin precisely at the transition between the section 44 and the spiral chamber 46, or in the spiral chamber 46. At its downstream end 56, the stator 50 is of a nature such that this only has a small radial cross section, for example a cross section of 3-80 mm2. In contrast, the rotor in the cylinder-shaped section can have a cross section of 20-180 mm2.

A blading 64 which in the present embodiment example is designed in a spiral-shaped manner is located on the outer side of the rotor 50. A first spiral 64 and a second spiral 64' are located on the rotor and are arranged offset to one another by 180°. The spirals extend around the rotor periphery by less than 360°. This can be recognised for example by the course of the spiral 64'. The pitch between two spirals, i.e. the distance between the spirals in the axial direction increases in the z-direction. Further examples for the rotor shape or for the arrangement of the blading on a rotor are to be found for example in EP 18 164 553.2 or WO 2011/054545 which are both adopted in their entirety as a constituent of this application.

The rotor can be constructed for example of metal, such as e.g. steel, titanium or other known biocompatible materials. Apart from a motor rotor which is drawn in for example as an element 66, a ring 68 which is magnetised in the z-direction and which on the one hand is part of a radial bearing 80 and on the other hand generates a magnetic flux of the rotor along the rotation axis 58 is located in the inside of the rotor. Furthermore, a flux concentrator 70 which concentrates the magnetic field of the flow generator 68 towards the rotation axis 58 and provides the rotor downstream with a magnetic field with a pronounced magnetic field component in the z-direction is located within the truncated-cone-shaped section 62 of the rotor. In some embodiment examples, the magnetic field component of the rotor which acts in the z-direction is evaluated by the sensor arrangement 90, in order to detect or evaluate a tilting of the rotor, i.e. a tilting of the rotation axis 58 with respect to the channel axis 42.

As already mentioned, the magnetic ring 68 is also a constituent of a passive magnet bearing 80. This further comprises a magnetic ring 82 which is arranged in the housing outside the fluid channel 40. The magnetic ring 82 is likewise axially polarised, i.e. its magnetic field is likewise aligned in the z-direction. The magnetic rings 68 and 62 are designed as a stable radial bearing so that the rotor has an equilibrium state inasmuch as the rotation axis 58 corresponds to the channel axis 42. Furthermore, the two rings are arranged axially offset to one another which effects an additional biasing of the rotor in the axial direction. The rings 82 and 68 can also be constructed from radially oppositely magnetised rings or be constructed as Halbach arrays. The sensor arrangement is then fed by the axially running magnetic scatter flux.

The distance between the downstream end 56 of the rotor 50 and the sensor arrangement 90 in the z-direction can be for example between 0.5 mm and 30 mm. In the present example the distance is 15 mm.

Although in the present embodiment example the rotor 50 is held upstream by a mechanical bearing, the upstream mechanical bearing in other embodiment examples can be replaced by a hydrodynamic bearing. The contact point for determining the tilting in the case of a hydrodynamic bearing would be given by a virtual contact point which is seated within the rotor.

A particularity of the pump put forward here is the free mounting of the downstream end of the rotor 50. As already mentioned, the downstream end is only restricted in its movement by a backup bearing. The backup bearing can be of a nature such that only pathological pump states are prevented, i.e. for example an abutting of the blading on the housing wall of the tubular section is prevented. Otherwise, the downstream end 56 within the ring 48 can describe free trajectories.

The signals which are recorded on the basis of the sensor arrangement 90 can be evaluated for example by control circuit (not represented) which is arranged in the pump or by way of an external pump control by way of a data lead which is integrated for example into the driveline.

Figure 3:
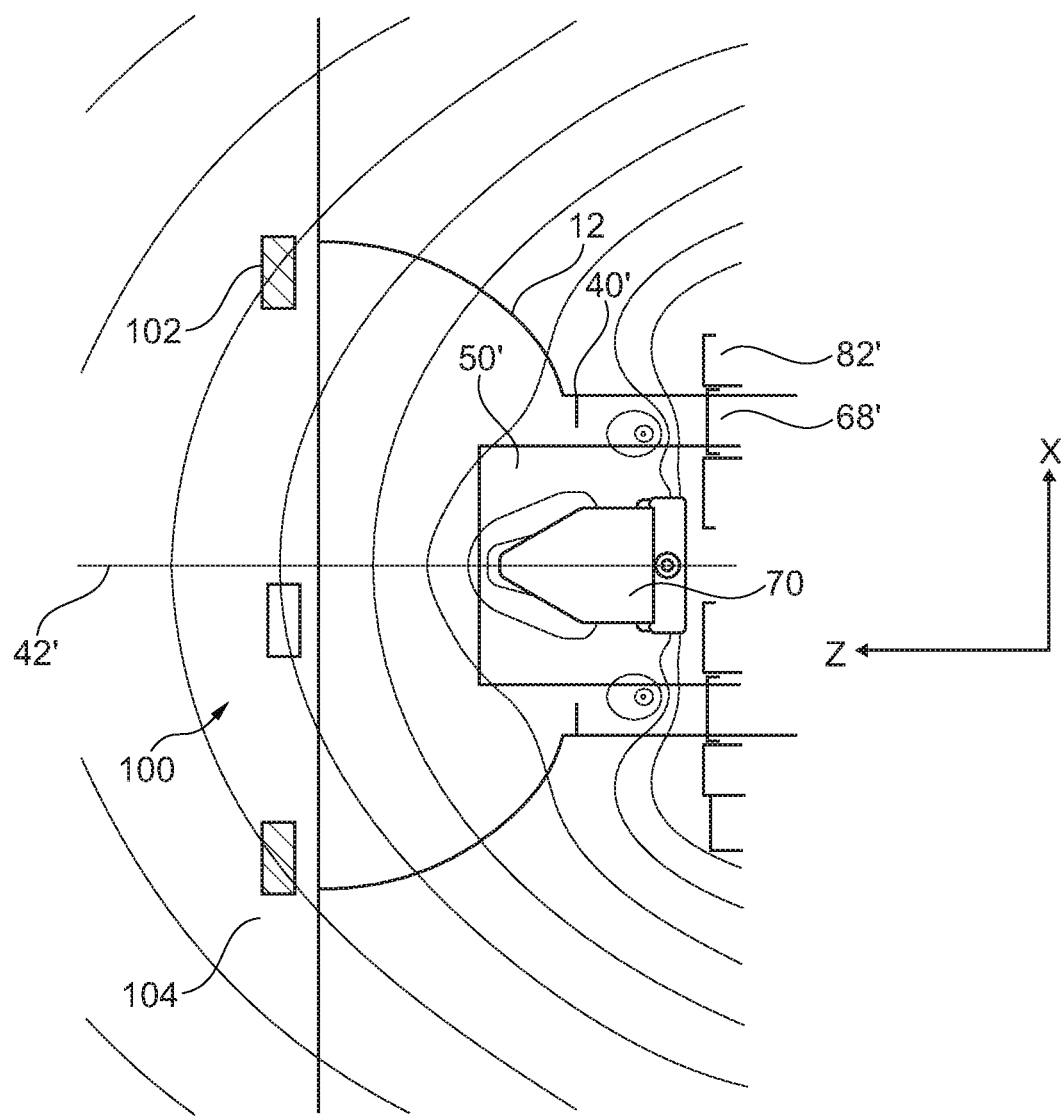
FIG. 3 is a magnetic field course between the rotor and the magnet which is arranged in the housing.

The magnetic field of the rotors represented in FIGS. 1 and 2, said magnetic field acting in the z-direction is to be represented by way of FIG. 3. Only a schematic fluid channel 40' is represented in FIG. 3 without dealing with the outlet chamber in more detail. By representation, the housing 12 in which the motor stator is arranged is recognised. Furthermore, a magnetic ring 82' is located downstream of the motor. The rotor 50' which in the present example is designed in a cylinder-shaped manner and comprises a motor rotor which interacts with the motor, a magnetic ring 68' and a flux concentrator 70' is located within the fluid channel 40'. The magnetic rings 68' and 82' are magnetised in the axial direction, i.e. in the z-direction. The magnetic orientation of the motor rotor which is magnetised essentially transversely to the z-direction can be distinguished from this. This orientation is much more suitable in order to be brought into rotation by the motor. Furthermore, magnetic potential lines which each represent a certain magnetic field strength can be recognised.

The magnetic field which acts downstream of the flux concentrator 70' is registered by the sensor arrangement 100 which comprises for example Hall effect sensors 102 and 104. The Hall effect sensors are arranged in a manner such that the z-component of the magnetic field is measured. The two sensors 102 and 104 are arranged symmetrically about the channel axis 42'. The distance can be for example between 2 and 15 mm along the x-direction, depending on the pump dimension. Alternatively or additionally, a further magnetic field sensor 105 can preferably be present along the channel axis 42'. The magnetic field sensor is of such a nature that the direction of a magnetic field vector can also be detected for example by way of a GMR sensor.

Figures 4A, 4B:
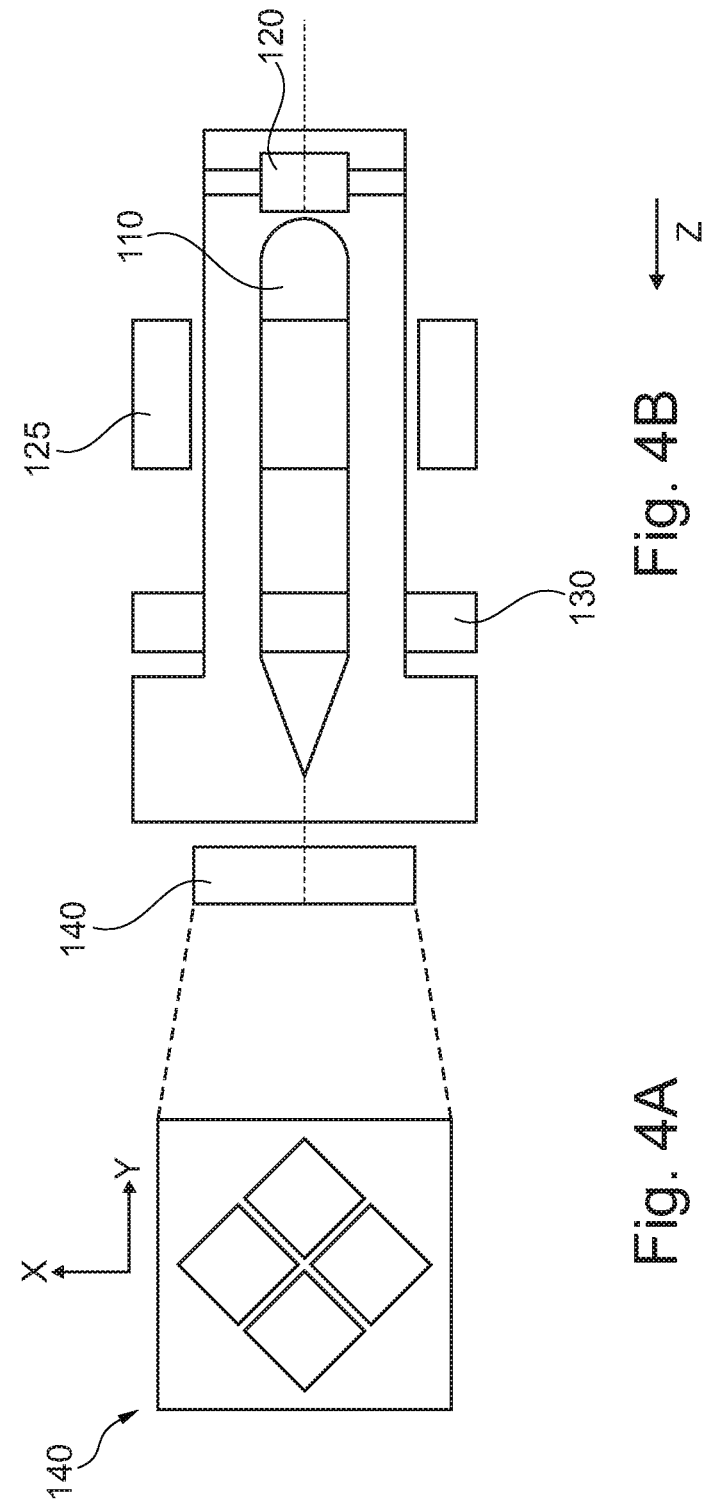
FIG. 4 a schematic representation of the sensor arrangement and the rotor.

A schematic arrangement of the sensors is represented for example in FIG. 4. In FIG. 4a, a system of four Hall effect sensors s illustrated, wherein these within the xy-axis are aligned around the middle point on the z-axis. Two sensors which are aligned along the x-axis and y-axis are kept in the same colour in FIG. 4a, in order to illustrate that these two sensors coupled to one another permit a differential measuring and thus a high measuring accuracy. The sensor arrangement along the z-direction is represented in FIG. 4b. The rotor 110 which lies on a mechanical barrier 120 in a point-like manner is also to be seen in a schematic manner. The rotor 110 is brought into rotation by the motor 125. The downstream end of the rotor 110 is radially mounted by a magnetic bearing 130. Magnets are arranged in the rotor itself and these are orientated in a manner such that a particularly large magnetic field component prevails in the z-direction. This can be evaluated by the sensor arrangement 140. The downstream end of the rotor 110 is axially distanced to the sensor arrangement 140. The sensor arrangement 140 itself is not located in the fluid channel, but within the housing. As can be recognised in FIG. 4A, the sensor arrangement comprises four Hall effect sensors which are arranged symmetrically about the channel axis. Two sensors which lie opposite one another along the channel axis can be brought together into a sensor pair. In this manner, the spatial angle of the tilting of the rotor can be determined.

Figure 5A:
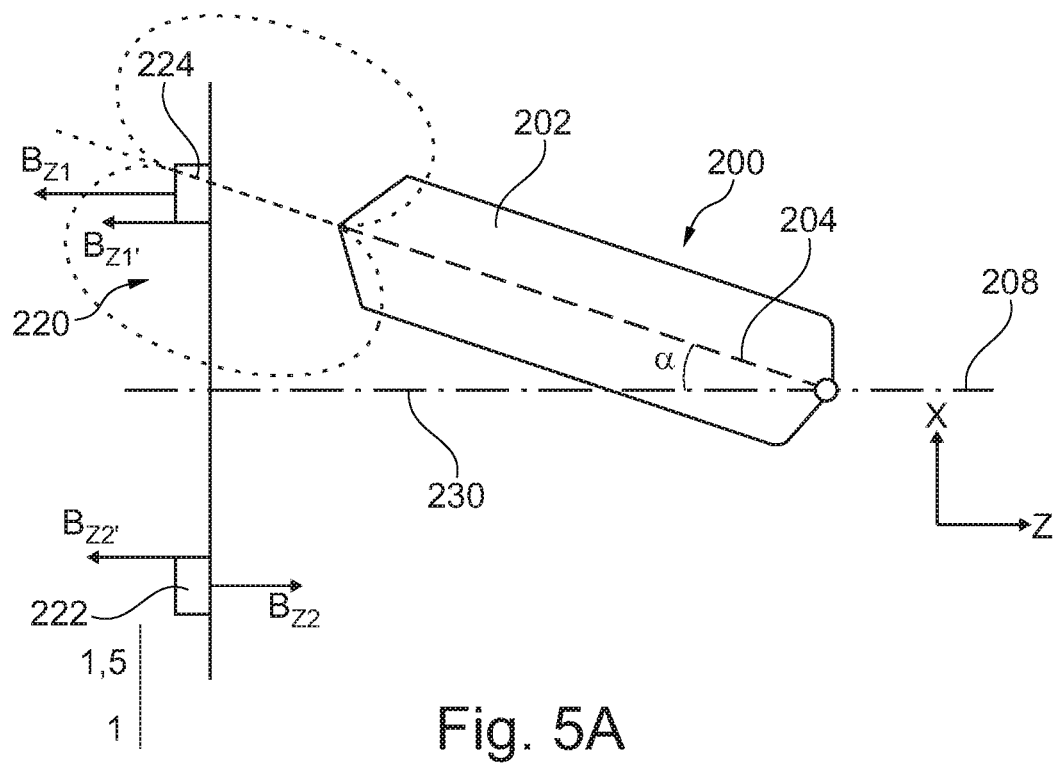
FIGS. 5a to c a tilting of a rotor as well as associated magnetic field course and trajectory of the downstream end of the rotor.
Figure 5B:
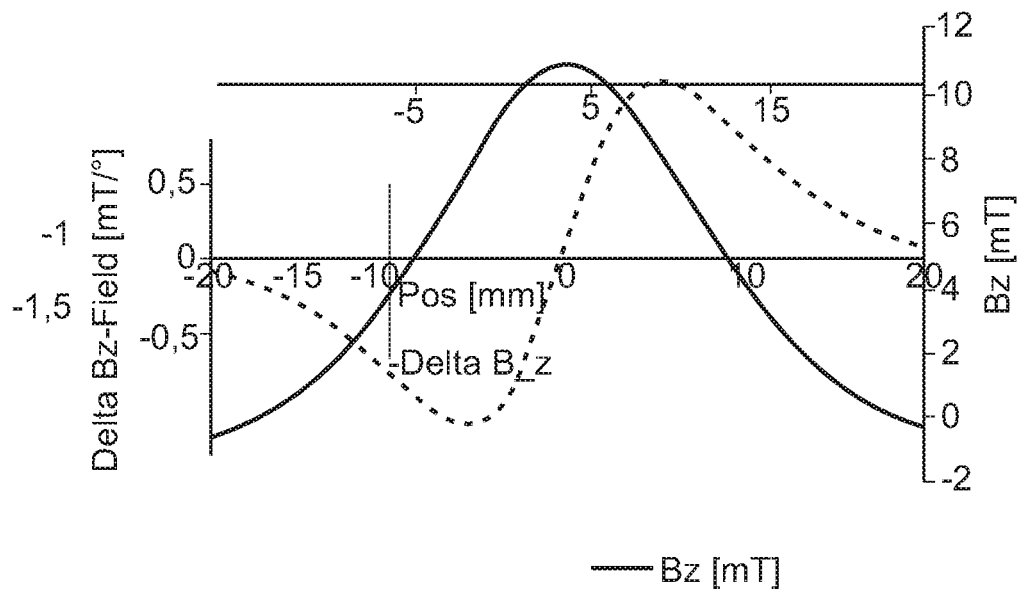

The evaluation of the magnetic field changes which are detected by the sensor arrangement are dealt with by way of FIG. 5. In FIG. 5A, a rotor 200 which has a rotor body 202 with a rotation axis 204 is schematically represented. The rotor further comprises a ball segment 206 which with a non-represented calotte segment forms a mechanical end bearing. The middle point of the ball 206 is the intersection point between the rotation axis 204 and a channel axis 208 which defines the fixed coordinate system. A sensor arrangement 220 with a first sensor 222 and with a second sensor 224 is located in the z-direction from the rotor 200 through the sensor arrangement. Although here only two sensors are represented, of course also more, for example three or four sensor can be used. In the represent state, the rotation axis 204 is tilted by an angle α with respect to the channel axis 208. The two sensors 222 and 224 assume identical or at least similar values of the magnetic field of the rotor in the non-tilted state of the rotor—on account of the radial symmetry of the magnetic field 230 which is produced by the rotor. This for example is evident by way of FIG. 5B. The unbroken curve of the magnetic field Bz which is represented there corresponds to the magnetic field Bz produced by the rotor along the x-axis in the non-tilted state. Inasmuch as the magnets do not produce a radially symmetrical magnetic field, the curve of the Bz component will deviate somewhat from the represented curve. This deviation however can be taken into account in the evaluation within the framework of a calibrating method. If now the rotor is tilted, as is indicated in FIG. 5A, then one of the two sensors perceives a significantly larger magmatic field, whereas the other sensor detects a significantly smaller magnetic field. This is represented schematically by way of the magnetic field Bz1 being greater and in its direction opposite to BZ2. In comparison to this, it can be recognised that the measured magnetic fields in the non-tilted state Bz1' and Bz2' are essentially equally large.

Following FIG. 5B, the sensors are placed at a distance to the rotation axis, in order to amplify the effect. The lines which are dashed in FIG. 5B provide the optimal position of the sensors along the x-axis for the suggested pump geometry at about 5 mm. Two sensors at this distance and which lie opposite one another along the x-axis with respect to the channel axis 208, as a differential sensor pair in the specified example provide somewhat more that 2 mT/° rotor tilting as a resolution. The optimum is dependent on the pump geometry. The differential measurement however functions for any distance to the axis of symmetry.

Only a momentary picture is represented in FIG. 5A, however the angle and the direction of the tilting of the rotor 200 changes over time. If for example the rotor is brought into rotation by the motor and delivers a fluid, then the rotor is tilted about an angle α in dependence on the produced flow. However, this angle α does not need to be constant, but for example can migrate in the xy-plane in a time interval. Furthermore, a movement of the rotation axis which is observable in the xy-plane can also be superimposed by a higher-frequency nutation movement.

With regard to the evaluation of the magnetic field changes and as to how the tilting can be used for estimating a flow, can be derived for example from WO2017/015 268 A1, WO2009/132 707 A1 or also Boening et al "Evolution of hydraulic radial forces on the impeller by the volute in a centrifugal rotary lock pump", Artificial Organ, Vol. 35, No. 8, 2011.

Figure 5C:
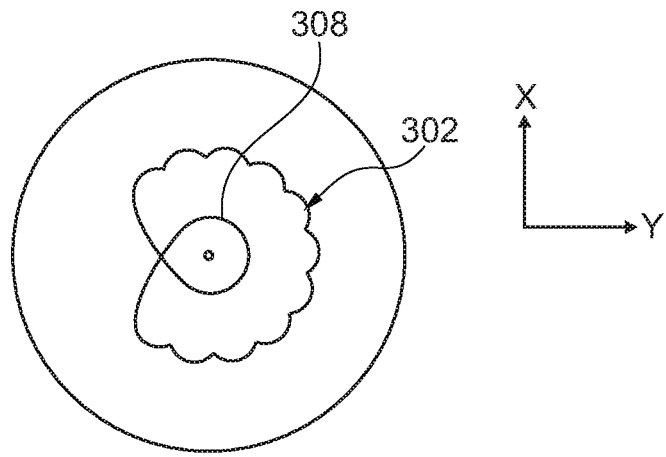

A trajectory of the downstream tip of the rotor 200 or the intersection point of the rotation axis in an xy-plane is represented in FIG. 5c. The trajectory 300 is a closed trajectory which example can indicate that the movements which act on account of the flow have harmonic or subharmonic relations with the rotation frequency of the rotor. This trajectory can then be superimposed by a nutation movement 302 which has a higher frequency than the frequency of the harmonic and subharmonic oscillations. The nutation movement can also serve for the detection of other effects such as the effects of wear, or deposits such as thrombi. The frequency spectrum of the movement of the rotation axis in the xy-plane, evaluated over time, can herewith be used in order to estimate the state of the pump. In this manner, on the one hand the flow can be estimated, a pressure estimated, the fluid viscosity estimated, suctioning detected, growing and entrained thrombi detected or appearances of wear on the bearings or on the motor or other deposits recognised. All changes of the equilibrium between the positive stiffness of the magnet bearing and negative stiffness between the motor stator and the motor magnet can be observed. These changes are manifested in the shift of the resonance frequency as well as of the equilibrium position. The effects of wearing can occur for example on the magnet bearing stator if this is heated too greatly by the motor stator.

Figure 6:
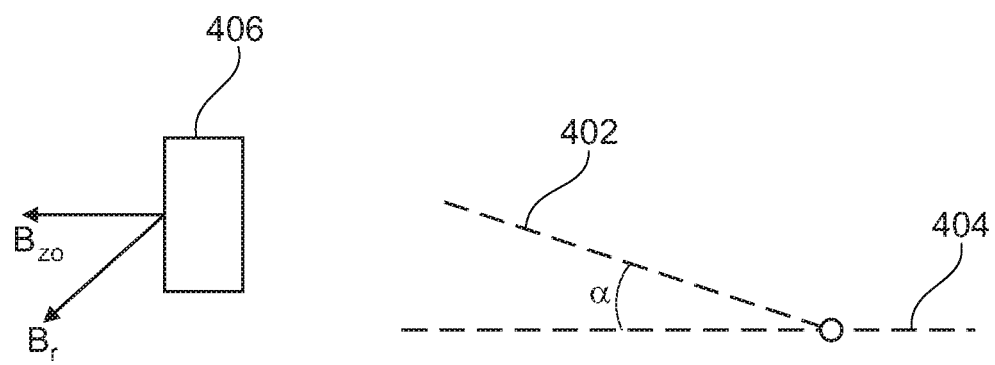
FIG. 6 alternative sensor arrangement and schematic functioning manner.

A further embodiment for detecting the tilting of the rotor is represented schematically in FIG. 6. Here it is only the rotation axis 402, the channel axis 404 and the angle α which is present between these which are represented. The sensor 406 which is axially distanced to the rotor is a magnetic field sensor which can detect the direction of the magnetic field vector in space. In the non-tilted state, at which the rotation axis and the channel axis lie coaxially to one another, the sensor 406 measures the one magnetic field vector Bz which in the ideal case is merely aligned along the z-axis. On tilting the rotor about the angle α, the sensor now measures a magnetic field vector Br which apart from a z-magnetic field component also has an x- and/or y-magnetic field component. The tilting of the rotor can be detected as a spatial angle by way of the evaluation of the vector direction.

In this manner, an estimation of the tilting and hence an estimation of the flow which is delivered by the pump can be made by way of a single sensor, for example an anisotropic magnetoresistive sensor (AMR, GMR or TMR). Several sensors for differentially measuring or for redundancy are possible and improve the measuring reliability given an increasing complexity.

Further embodiment examples result in an obvious way and manner for the person skilled in the art.

To clarify the use of and to hereby provide notice to the public, the phrases "at least one of <A>, <B>, . . . and <N>" or "at least one of <A>, <B>, . . . or <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A pump comprising:
   a housing with an upstream inlet and an downstream outlet and a fluid channel with a channel axis, said fluid channel being arranged between the inlet and the outlet;
   a rotor with an upstream and a downstream end, wherein the rotor is arranged in the fluid channel, comprises a blading for the delivery of the fluid, and is mounted upstream by a mechanical or hydrodynamic bearing;
   a motor which is arranged in the housing, so that the rotor can be brought into rotation about a rotation axis;
   a passive magnetic bearing comprising a magnetic ring that is arranged in the housing outside of the fluid channel;
   a sensor arrangement for detecting an inclination of the rotor axis of the rotor, wherein the sensor arrangement is arranged downstream from the rotor; and
   wherein the pump is an axial pump.

2. The pump of claim 1, wherein the sensor arrangement is configured so that a magnetic field of the rotor which runs in the direction of the channel axis is measurable.

3. The pump of claim 1, wherein the sensor arrangement comprises at least one magnetoresistive sensor or a Hall effect sensor.

4. The pump of claim 1, wherein the sensor arrangement comprises at least three sensors for detecting a magnetic field.

5. The pump of claim 4, wherein the sensor arrangement is configured for differentially measuring the magnetic field.

6. The pump of claim 1, wherein the passive magnetic bearing is a radial bearing.

7. The pump of claim 1, wherein the rotor comprises a magnetic flux concentrator.

8. The pump of claim 7, wherein the rotor upstream of the flux concentrator comprises a flux generator.

9. The pump of claim 1, wherein the rotor tapers towards its downstream end.

10. The pump of claim 1, wherein a mechanical backup bearing for the downstream end of the rotor is arranged on the housing.

11. The pump of claim 1, wherein the fluid channel merges into an outlet chamber and an outlet axis of the outlet is inclined by an angle with respect to the channel axis.

12. The pump of claim 1, wherein the pump is designed for the axial delivery of the fluid or the blading of the rotor is designed in a spiral-shaped manner.

13. The pump of claim 1, wherein the sensor arrangement is connected to an evaluation unit which evaluates the inclination of the rotor.

14. The pump of claim 1, wherein the sensor arrangement resolves an inclination of the rotation axis with respect to the channel axis with an accuracy of 0.05°.

15. The pump of claim 1, wherein the sensor arrangement comprises at least four or more sensors for detecting a magnetic field.

16. The pump of claim 1, wherein the rotor comprises a magnetic flux concentrator which is arranged in the region of the downstream end of the rotor.

17. The pump of claim 7, wherein the rotor upstream of the flux concentrator comprises a flux generator, wherein the flux generator forms part of the passive magnet bearing.

18. The pump of claim 1, wherein the fluid channel merges into an outlet chamber and an outlet axis of the outlet is inclined by an angle with respect to the channel axis running essentially perpendicularly thereto.

19. The pump of claim 1, wherein the sensor arrangement is connected to an evaluation unit which evaluates the inclination of the rotor in a time-resolved manner.

* * * * *